United States Patent [19]

Capuano et al.

[11] Patent Number: 5,565,172
[45] Date of Patent: Oct. 15, 1996

[54] HYDRAULIC FLUID VAPOR SENSOR

[75] Inventors: Italo A. Capuano, Orange; Kenneth E. Creasy, Wallingford both of Conn.

[73] Assignee: Olin Corporation, Cheshire, Conn.

[21] Appl. No.: 259,107

[22] Filed: Jun. 13, 1994

Related U.S. Application Data

[62] Division of Ser. No. 43,708, Apr. 8, 1993, Pat. No. 5,342,786.

[51] Int. Cl.$^6$ ...................................................... G01N 30/02
[52] U.S. Cl. ............................. 422/83; 422/78; 422/80; 422/82; 436/103; 436/104; 436/139; 436/142; 436/155; 436/161; 73/23.35; 73/23.42; 73/863.11; 73/864.83
[58] Field of Search ...................... 422/78, 83, 82, 422/84, 89, 98, 54, 90; 436/137, 139, 103, 104, 142, 155, 161; 73/23.35, 23.42, 863.11, 863.12, 864.83

[56] References Cited

U.S. PATENT DOCUMENTS

| | | | |
|---|---|---|---|
| 3,762,878 | 10/1973 | Villalobos | 436/143 |
| 3,996,004 | 12/1976 | Fine et al. | 436/110 |
| 4,198,208 | 4/1980 | Lerner et al. | 436/159 |
| 5,116,764 | 5/1992 | Annino et al. | 436/161 |
| 5,361,626 | 11/1994 | Colligan et al. | 73/40.7 |

OTHER PUBLICATIONS

DeLijser et al. CA 118(24):240057xX, publication year 1993.
DeLijser et al. "Reductive Pyrolysis of Organic phosphorous Compounds" ACS vol. 33 No. 1 Mar. 28, 1993 87–89.
DeLigser et al. article "Reductive Pyrolysis of Organic Phosphorus Compounds", Mar. 22, 1993.
Article "Electrochemical Study of Aluminum (VI) in Aqueous Soulution of Tri-n-butyl Phosphate" by D. Krznaric, B. Cosovic, and M. Branica, published in J. Electroanal. Chem. 33(1971) pp. 61–68.
Article "UV Photoelectron and ab Initio Quantum Mech. Characterization of Nucleotides; The Valence Electronic Structures of 2'-deoxycytidine-5'-phosphate" by K. Tasaki et al., published in J. Am. Chem. Soc. 1990, vol. 112, pp. 538–548.
"Functional Fluids for Industry, Transportation & Aerospace", edited by M. William Ranney; Noyes Data Corp. 1980, pp. 147–195.
"Intro to Hydraulic Fluids", R. E. Hatton, Reinhold Publishing Corp., New York, 1961, pp. 190–211.
2 Material Safety Data Sheets (a) Chevron Hyjet IV-A, Rev. G, May 10, 1990; and (b) Monsanto Skydrol 500B-5 Fire Resistant Hydraulic Fluid.

*Primary Examiner*—James C. Housel
*Assistant Examiner*—Rachel Heather Freed
*Attorney, Agent, or Firm*—William A. Simons; H. Samuel Kieser

[57] ABSTRACT

A method and apparatus for detecting the presence of a vapor of an alkyl ester of phosphoric acid, particularly tributylphosphate, in ambient air. A sample of ambient air is heated to convert any alkyl ester of phosphoric acid to an alkene. The heated sample of air is then passed to a sample loop. Carrier air periodically carries a fixed volume of sample from the sample loop through a chromatographic column to a photoionization detector which detects the presence and amount of the alkene in the sample.

9 Claims, 1 Drawing Sheet

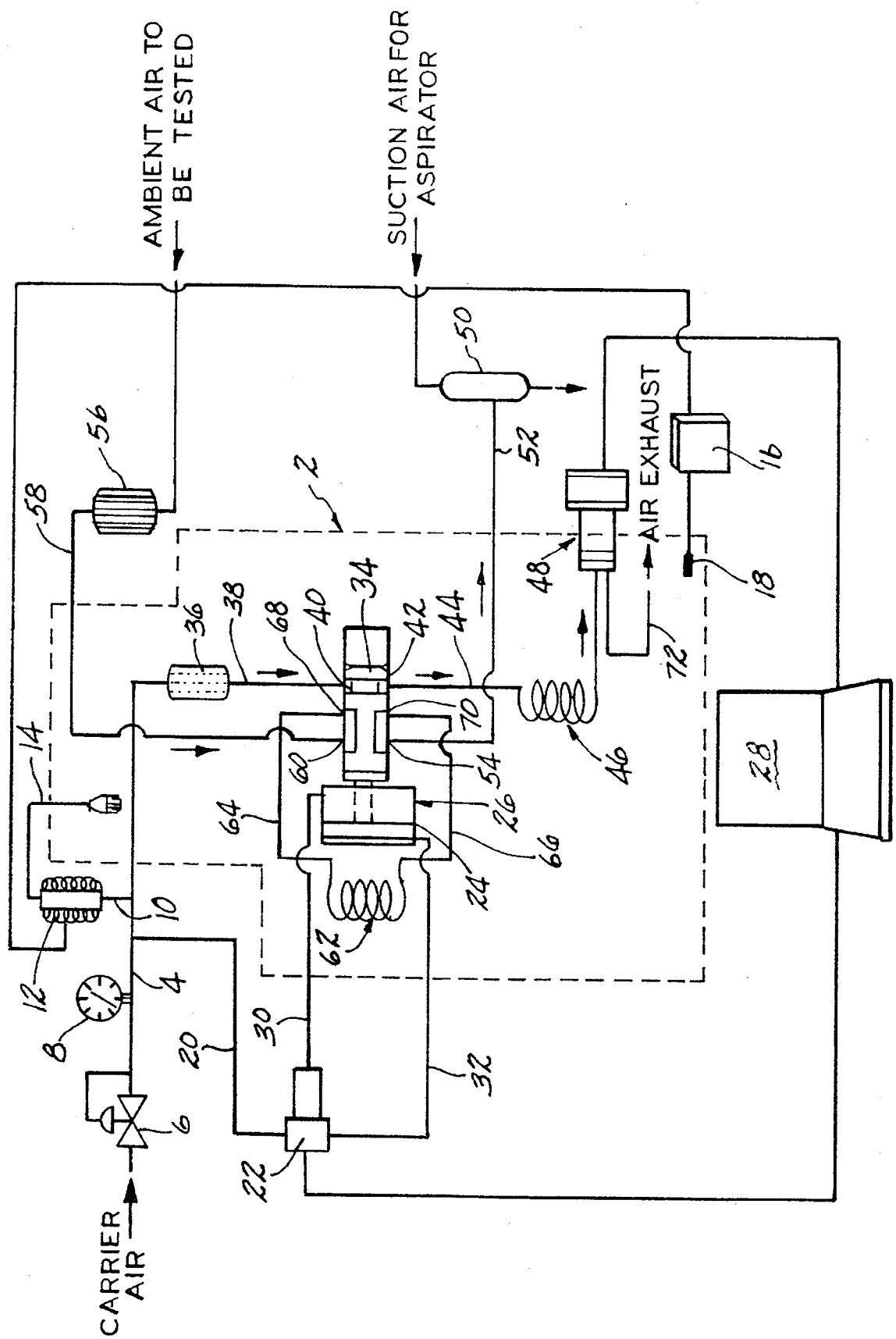

HYDRAULIC FLUID VAPOR SENSOR

This application is a division of application Ser. No. 08/043,708 filed Apr. 8, 1993, now U.S. Pat. No. 5,342,786, which is incorporated herein by reference in its entirety.

BACKGROUND OF THE INVENTION

This invention relates generally to the sensing of fluid vapors. More particularly, this invention relates to the sensing of vapors from alkyl esters of phosphoric acid which are present in hydraulic fluids.

Alkyl esters of phosphoric acid, and particularly, tributylphosphate, are common components of hydraulic fluids especially of the type used in aircrafts. As the vapors of such components may be toxic, there is a need for a simple and reliable sensor to measure the presence of such vapors in the ambient air, particularly at stratetic locations within an aircraft so that any leakage of the vapor into ambient air can be detected and appropriate measures be taken before any adverse effect upon personnel within the aircraft.

The sensor should be capable of measuring a concentration of such vapors in the air as low as 400 parts per billion by volume. In addition, the sensor should be capable of forming very rapid analysis (less than 3 minutes) and require little routine service and maintenance over a long period of time.

The sensor also must be selective to the particular alkyl ester of phosphoric acid present in the hydraulic fluid. Accordingly, the sensing process must not be interfered with by any other trace chemical impurities that may be present in the ambient air, particularly that of the aircraft. Several of the potential chemicals which could present interference with the sensor include air ($N_2$ and $O_2$), water, sulfur dioxide, ozone, nitromethane, nitromethane, hydrogen chloride, and carbon dioxide.

The monitoring of such vapors, especially tributylphosphate, presents many obstacles. Sampling of tributylphosphate vapor in the air under normal conditions is virtually impossible since it absorbs on the surface of the sampling system and requires considerable time to completely desorb. Moreover, tributylphosphate has a very high boiling point (269° C.), at which temperature it decomposes.

SUMMARY OF THE INVENTION

In view of the above, it is an object of the present invention to provide a method and apparatus for the sensing of an alkyl ester of phosphoric acid present in ambient air.

More particularly, it is an object of the present invention to provide a method and apparatus for the sensing of tributyl phosphate vapor in ambient air.

More specifically, it is an object of the present invention to provide a method and apparatus for the sensing of an alkyl ester of phosphoric acid present as vapor in ambient air and which is selective to the particular alkyl ester desired to be sensed and not interfered with other trace chemical impurities.

These and other objects of the present invention may be achieved in accordance with the present invention through the provision of a method for detecting the presence of a vapor of an alkyl ester of phosphoric acid which comprises taking a sample of ambient air and treating the sample to convert the alkyl ester of phosphoric acid to an alkene. The presence of the alkene in the sample is then determined.

In accordance with the present invention, an apparatus for detecting the presence of a vapor of an alkyl ester or phosphoric acid in ambient air may comprise means for taking a sample of ambient air, and means for converting the vapor of the alkyl ester of phosphoric acid into an alkene. Means are provided for determining the presence of the alkene in the treated sample.

The invention may be more understood by reference to the following detailed description and to the accompanying drawings in which:

BRIEF DESCRIPTION OF THE DRAWINGS

FIG. 1 is a schematic representation of an apparatus in accordance with the present invention.

DETAILED DESCRIPTION

FIG. 1 is a schematic drawing showing an apparatus in accordance with the present invention which is capable of detecting the presence of a vapor of an alkyl ester phosphoric acid in ambient air. The apparatus is useful for many specific types of vapors, but is particularly useful for the sensing of tributylphosphate which is a component of hydraulic fluids used in aircrafts. Specific examples of hydraulic fluid which contain tributylphosphate and which is used in aircrafts include Hyjet IV-A manufactured by Chevron and Skydrol LD-4 and Skydrol 500-B-4 manufactured by Monsanto.

Referring to FIG. 1, the apparatus includes a sensor housing 2 indicated by the dotted lines. Carrier air under pressure from a suitable source is supplied through line 4 into the housing 2 through a pressure regulating valve 6 which may be mounted external of the housing 2 downstream of the valve 6. A pressure gauge 8 may be positioned in the line 4 downstream of the valve 6 for monitoring the pressure of the carrier air. A portion of the air from line 4 is bled off through a line 10 to an electrical heater 12, external of the sensor housing 2, to provide heated air through line 14 into the interior of the sensor housing 2 so that the sensor housing 2 provides a heated enclosure. A proportional temperature controller 16, which may be external of the housing 2 has a temperature sensor 18 mounted within the sensor housing 2 to sense the temperature therein and provide feedback to the electrical heater 12 to maintain the interior of the sensor housing at a constant temperature. The temperature within the housing 2 should be maintained at a temperature high enough above ambient so that changes in the ambient temperature will not have a significant effect upon the interior temperature. A temperature of from about 60° to 70° C. may be used as an example.

A portion of a carrier air is also bled off through a line 20 to an electrically actuated solenoid valve 22. The solenoid 22 serves to direct the bled air to either side of the diaphram 24 of a sample valve 26 positioned within the sensor housing 2 to cause the actuation thereof. The solenoid valve 22 is operated by electrical signals from a console unit 28 to direct air through either air line 30 or air line 32 going to opposite sides of the diaphram 24 of the sample valve 26.

The sample valve 26 may be a 6-port valve with the piston element 34 thereof moveable between a sample gathering position as shown in FIG. 1 and a sampling position wherein the piston element is moved to the right from its position shown in FIG. 1.

The carrier air passes into the sensor housing 2 through line 4 and passes through a carbon air filter 36. The air exits the filter through a line 38 attached to one port 40 of the sampling valve 24. In the sample-gathering position, the piston 34 of the sample valve 26 connects the incoming carrier air from line 38 with an outlet port 42 connected to a line 44. The line 44 is connected to a chromatographic column 46 which in turn is connected to a detector 48.

An aspirator 50, passing air therethrough, draws a suction through line 52 attached to a port 54 of the sample valve 26.

The ambient air which is to be tested for the presence of the alkyl ester of phosphoric acid is drawn through a heated reactor 56. This heated reactor 56, which may be positioned immediately on the outside of the sensor housing 2, is used to convert the vapor of an alkyl ester of phosphoric acid into its alkene component for sampling purposes. The heated reactor 56 is a conventional type hot air heater. For example, the heater may be a 1000 Watt Air heater of the type manufactured by Hotwatt, Inc. The heater relies upon the moisture vapor in the ambient air to provide the water necessary for the hydrolosis of the alkyl ester of phosphoric acid into its alkene component. By way of example, one alkyl ester of phosphoric acid for which this invention is particularly adapted is tributylphosphate. As shown by the following chemical equations, the hydrolysis of the tributylphosphate molecule produces butene:

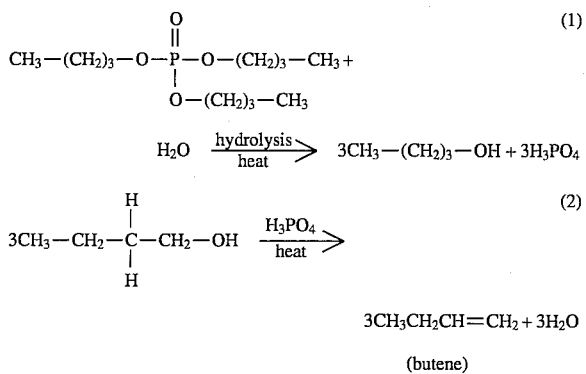

(butene)

The moisture from the ambient air provides the water which is consumed in the first step chemical reactions. Thus, any tributylphosphate in the air entering the heated reactor 56 exits from the reactor 56 through line 58 as butene which, under ordinary conditions, is a gas.

The temperature of the reactor and resident time of the ambient air should be sufficient to ensure that the alkyl ester is broken down into its alkene. Preferably, the temperature is maintained at at least 250° C. The residence time may be relatively short, in the order of less than a second. Line 58 containing the treated sample air extends from the reactor 56 into the sensor housing 2 and is connected to the port 60 of the sample valve 26.

A sample loop 62, preferably a coil of tubing, is provided which can contain a predetermined volume of reacted ambient air for testing. The inlet and outlet lines 64 and 66 to and from the sample loop 62 are connected to the ports 68 and 70 respectively of the sample valve 26 as indicated in FIG. 1. Thus, with the sample valve in its sample-gathering position, the aspirator 50 constantly draws sample air through the reactor 56, through line 58 into the sample valve 26, out of the sample valve 26 through line 64, through the sample loop 62 back into the sample valve 26 through line 66 and out through line 52 to the aspirator 50.

At predetermined intervals, which may be preprogrammed by the controller 28, when it is desired to test the sample of ambient air, a signal is sent to the solenoid valve 22 to cause the valve 22 to switch to permit air to flow through line 32 to actuate the sample valve 26 and cause the piston element 34 thereof to move to the right as viewed in FIG. 1. In this position, the carrier air connected with line 64 going to the sample loop 62. The output line 66 from the sample loop 62 is connected to the line 44 running to the chromatographic column 46. The line 58 from the reactor 56 and the line 52 to the aspirator 50 are blocked by the sample valve 26 during this interval.

During this testing period, the carrier air flows through the sample loop 62 carrying a fixed volume of the sample of ambient air from the sample loop 62 through the chromatographic column 46 and detector The chromatographic column renders the detector 48 selective by spatially separating the butene, or other alkene, from the other components of the ambient air as it passes through the column. The column may consist of a coil of packed tubing having a medium therein which will cause the spatial separation of the alkene such as butene. By way of example the column may comprise a coil of tubing packed with Kel-F® oil, manufactured by Minnesota Mining and Manufacturing Company, deposited on diatomaceous earth. The tubing may be aluminum and vary in length, although a 10 foot length has been used successfully.

The detector 48 is adapted to give an electronic output proportional to the amount of butane present in the sample tested. A number of different types of detectors may be suitable for the detection of butene or other alkenes such as a flame ionization detector (FID) a photoionization detector (PID) and a discharge ionization detector (DID). The FID detector is generally not satisfactory for use in aircraft applications because of its flame. A DID detector also is generally inadequate because it possesses relatively little selectivity. Additionally, both the DID and FID detectors require bottled gas such as helium and hydrogen, which also makes these impractical for use in aircraft. Accordingly, it is preferred to use a PID detector because of its considerable selectivity. The detector may be any commercially available photoionization detector. A suitable detector is a 10.2 electron volt lamp detector manufactured by H.N.U. Systems Inc. The output signal from the detector 48 may be sent to the controller 28 or other device to be processed to provide an alarm when the detected concentration is over a minimum amount, an analog or digital readout, as well as to provide a print out if desired.

The detector may be calibrated by passing an air sample through the system containing a known amount of tributylphosphate and observing the detector signal output and then determining a correlation between the electrical signal output of the detector and the amount of tributylphosphate in the sample air.

The sample valve 26, sample loop 62, the chromatographic column 46 and detector 48 are all contained within the sensor housing 2 which is maintained at a constant temperature through the electric heater 12 and proportional temperature controller 16. Thus, the temperature of the sample will remain constant and provide consistency between the vapor samples.

During the sample-gathering period, when no detection is being carried on, the carrier air line 4 and 38 is connected to the outlet line 44 from the sample valve 26. This provides a supply of pressurized air through the chromatographic column 46 and detector 48 and then through the exhaust 72 from the detector 48 to purge the detection system.

While the invention has been described above with reference to a specific embodiment thereof, it is apparent that many changes, modifications, and variations can be made without departing from the concept disclosed herein. Accordingly, it is intended to embrace all such changes, modifications, and variations that fall within the spirit and broad scope of the appended claims. Any patent or patent applications cited herein is incorporated by reference in its entirety.

What is claimed is:

1. An apparatus for detecting the presence of a vapor of an alkyl ester of phosphoric acid in ambient air consisting essentially of:

a. means for taking a sample of ambient air, b. means for heating said sample to convert any alkyl ester of phosphoric acid to an alkene, and c. means for detecting the presence of said alkene in said heated sample.

2. The apparatus of claim 1 wherein said means for detecting includes a photoionization detector.

3. The apparatus of claim 2 wherein said means for detecting also includes a chromatographic column through which said sample passes before it passes through said photoionization detector.

4. The apparatus of claim 1 wherein said alkyl ester of phosphoric acid is tributyl phosphate and said alkene is butane.

5. An apparatus for detecting the presence of a vapor of an alkyl ester of phosphoric acid in ambient air consisting essentially of:

a. means for taking a sample of ambient air;

b. means for heating said sample to convert any alkyl ester of phosphoric acid in said sample into an alkene;

c. a sample loop for containing a fixed volume of said heated sample;

d. detector means for detecting the presence of any alkene in said sample; and e. means for periodically causing a carrier fluid to carry a predetermined volume of said sample from said sample loop to said detector.

6. The apparatus of claim 5 wherein said detection means comprises a chromatographic column and a photoionization detector, said sample passing through said column before said photoionization detector.

7. The apparatus of claim 6 further comprising means for passing said carrier fluid through said column and detector during the period said sample is not being carried to said column and detector.

8. The apparatus of claim 7 further including an aspirator for drawing said sample of ambient air into said sample loop.

9. The apparatus of claim 7 further including a housing in which said sample loop, chromatographic column and detector are mounted and means for maintaining the interior of said housing at a constant temperature.

* * * * *